(12) United States Patent
Griner et al.

(10) Patent No.: US 7,935,120 B2
(45) Date of Patent: May 3, 2011

(54) POSTERIOR FEMUR ROUGH CUT GUIDE FOR MINIMALLY INVASIVE KNEE ARTHROPLASTY

(75) Inventors: Adam M. Griner, Columbia City, IN (US); Kim Bertin, Salt Lake City, UT (US); Richard Berger, Chicago, IL (US); Ron Donkers, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1046 days.

(21) Appl. No.: 11/118,168

(22) Filed: Apr. 29, 2005

(65) Prior Publication Data

US 2006/0004374 A1    Jan. 5, 2006

Related U.S. Application Data

(60) Provisional application No. 60/566,801, filed on Apr. 30, 2004.

(51) Int. Cl.
*A61B 17/56* (2006.01)
(52) U.S. Cl. .......................................... 606/88; 606/86 R
(58) Field of Classification Search .................... 606/62, 606/64, 88
See application file for complete search history.

(56) References Cited

U.S. PATENT DOCUMENTS

| | | | |
|---|---|---|---|
| 4,567,885 A * | 2/1986 | Androphy | 606/88 |
| 4,759,350 A * | 7/1988 | Dunn et al. | 606/82 |
| 5,122,144 A | 6/1992 | Bert et al. | |
| 5,226,915 A * | 7/1993 | Bertin | 623/20.15 |
| 5,234,433 A | 8/1993 | Bert et al. | |
| 5,445,642 A | 8/1995 | McNulty et al. | |
| 5,458,645 A | 10/1995 | Bertin | |
| 5,474,559 A | 12/1995 | Bertin et al. | |
| 5,520,695 A | 5/1996 | Luckman | |
| 5,540,696 A | 7/1996 | Booth, Jr. et al. | |
| 5,562,675 A | 10/1996 | McNulty et al. | |
| 5,743,915 A | 4/1998 | Bertin et al. | |

(Continued)

OTHER PUBLICATIONS

Laskin, "Ten Steps to an Easier Revision Total Knee Arthroplasty", The Journal of Arthroplasty; vol. 17 No. 4 Suppl. 1; pp. 78-82; 2002.*

(Continued)

*Primary Examiner* — Eduardo C Robert
*Assistant Examiner* — Julianna N. Harvey
(74) *Attorney, Agent, or Firm* — Baker & Daniels LLP

(57) ABSTRACT

A method of preparing the proximal tibial and distal ends of the femur for the implantation of prosthetic components, including the steps of exposing the joint; resecting the distal end of the femur; resecting the tibia; and making a preliminary rough cut of a posterior portion of the pair of condyles. The rough cut is made by positioning a guide on the distal end of the femur and severing a small piece of the posterior portion of the pair of condyles. The rough cut is made prior to the step of resecting the tibia. The method may include finishing the femur by severing and removing a final piece of the posterior portion of the pair of condyles. The small piece removed in the preliminary rough cut step is sized to preserve enough of posterior portion to permit the removal of the final piece.

16 Claims, 12 Drawing Sheets

U.S. PATENT DOCUMENTS

| | | | |
|---|---|---|---|
| 5,925,049 A * | 7/1999 | Gustilo et al. | 606/82 |
| 6,077,270 A * | 6/2000 | Katz | 606/88 |
| 6,296,646 B1 | 10/2001 | Williamson | |
| 6,770,077 B2 | 8/2004 | Van Zile et al. | |
| 2002/0173797 A1 | 11/2002 | Van Zile et al. | |
| 2003/0158606 A1 | 8/2003 | Coon et al. | |
| 2003/0171757 A1 | 9/2003 | Coon et al. | |
| 2003/0204263 A1 | 10/2003 | Justin et al. | |
| 2003/0220697 A1 | 11/2003 | Justin et al. | |
| 2003/0225457 A1 | 12/2003 | Justin et al. | |
| 2004/0039395 A1 | 2/2004 | Coon et al. | |
| 2004/0073315 A1 | 4/2004 | Justin et al. | |
| 2004/0153066 A1* | 8/2004 | Coon et al. | 606/54 |
| 2004/0153162 A1* | 8/2004 | Sanford et al. | 623/20.3 |
| 2004/0158255 A1 | 8/2004 | Justin et al. | |

OTHER PUBLICATIONS

Nexgen Complete Knee Solution, Micro-Mill Instrumentation Surgical Technique.

Nexgen Instrument Options.

Nexgen Complete Knee Solution, Intramedullary Instrumentation Surgical Technique for Cruciate Retaining Knees.

Nexgen Complete Knee Solution, Intramedullary Instrumentation Surgical Technique.

Nexgen Complete Knee Solution, Multi-Reference 4-in-1 Femoral Instrumentation, Posterior Reference Surgical Technique.

* cited by examiner

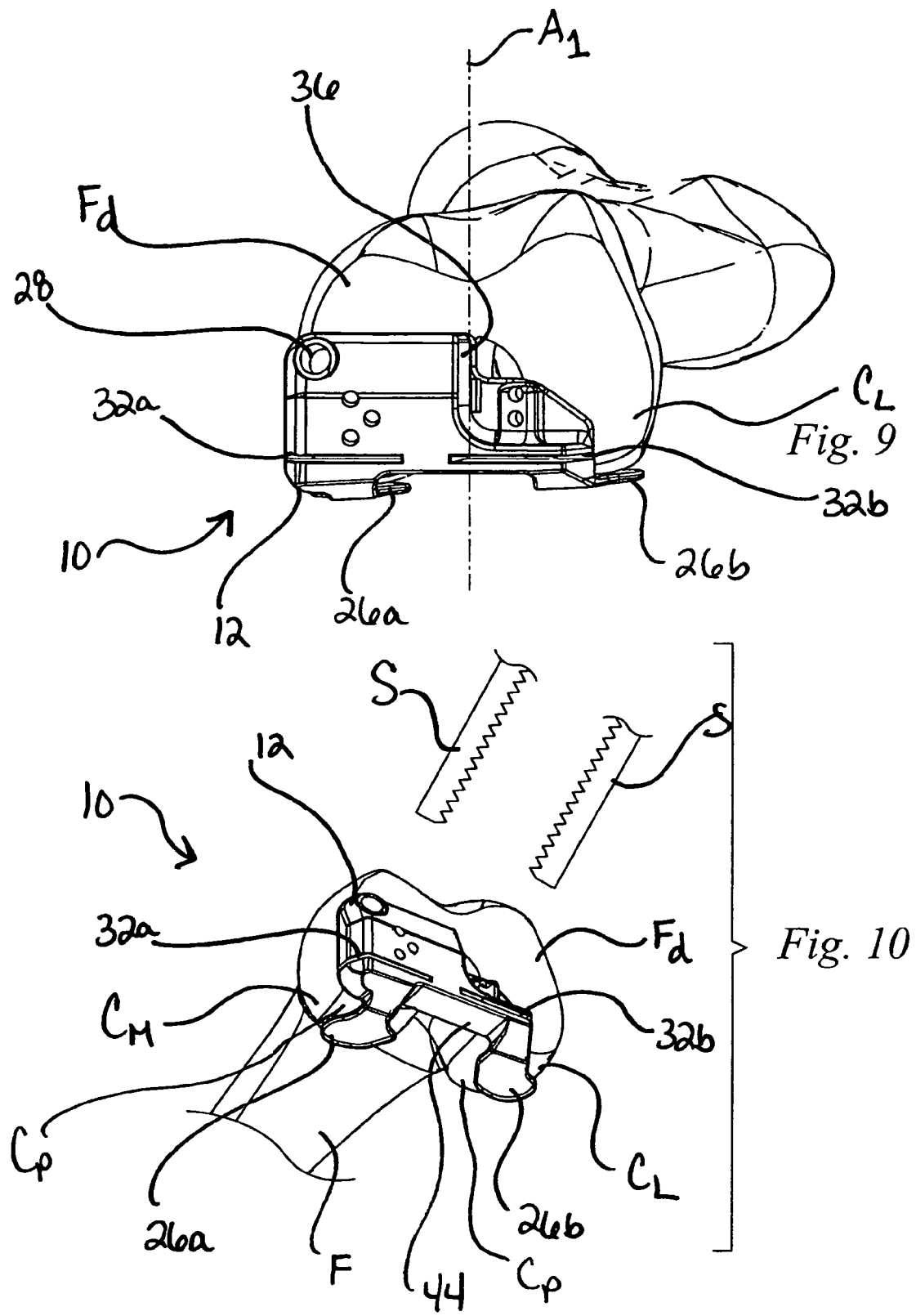

POSTERIOR FEMUR ROUGH CUT GUIDE FOR MINIMALLY INVASIVE KNEE ARTHROPLASTY

PRIORITY REFERENCE

This application claims the benefit of priority under 35 U.S.C. §119(e) to provisional application Ser. No. 60/566,801, filed in the name of Adam M. Griner on Apr. 30, 2004 and entitled POSTERIOR FEMUR ROUGH CUT GUIDE FOR MINIMALLY INVASIVE KNEE ARTHROPLASTY.

BACKGROUND

The present invention relates to knee arthroplasty, and in particular, to an instrument and minimally invasive method for preparing a knee joint to receive the components of a knee prosthesis.

Orthopedic procedures for the replacement of all, or a portion of, a patient's joint have been developed over the last thirty years. Currently, the procedures used to prepare the bone and seat the implants are generally referred to as open procedures. For the purposes of this discussion, the term "open procedure" will refer to a procedure wherein an incision is made through the skin and underlying tissue to fully expose a large portion of the particular joint surface. In both total and unicondylar knee arthroplasty, the typical incision for an open procedure is about 8-10 inches long. After the initial incision in the skin, the internal wound may be enlarged to fully expose the areas to be prepared. While this approach provides surgeons with an excellent view of the bone surface, the underlying damage to the soft tissue, including the muscles can lengthen a patient's rehabilitation time after surgery. While the implants may be well fixed at the time of surgery, it may be several weeks or perhaps months before the tissues violated during surgery are fully healed.

Minimally invasive procedures have been developed to reduce both the incision size and the damage to soft tissue, thereby shortening a patient's rehabilitation time. One such procedure is described in The Zimmer MIS™ Quad-Sparing™ Surgical Technique for Total Knee Arthroplasty (NEXGEN® Complete Knee Solution), a surgical procedure for minimally invasive knee arthroplasty available from The Zimmer Institute of Warsaw, Ind. and attached hereto as Appendix A. Total knee replacement procedures generally involve the consecutive steps of making an incision and exposing the joint, resecting the distal end of the femur, resecting the proximal end of the tibia, sizing the femur and establishing external rotation, finishing the femur, sizing and finishing the tibia, performing trial reductions, and implanting the prosthesis components. Although effective, it is known that the joint space within which the surgeon must work is restricted and the cutting and removal of bone can be a challenging task when working in this small joint space.

There is a need for a method and an instrument that can be used to create additional space at the surgical site and facilitate the steps in the preparation of the knee joint to receive the components of a knee prosthesis

SUMMARY OF THE INVENTION

The present invention provides a method and device for performing a posterior femoral rough cut in the distal femur during a minimally invasive knee arthroplasty. The rough cut is performed prior to resecting the tibia to create more space in the joint thereby providing improved visibility of the surgical site and easing the removal of cut portions during tibial resecting.

In one form, the present invention provides a method of preparing the tibial proximal end and the distal end of the femur for the implantation of prosthetic components. The method comprises the steps of exposing the joint, resecting the distal end of the femur, resecting the tibia, and making a preliminary rough cut of a posterior portion of the pair of condyles. The rough cut may be made by positioning a rough cut guide on the distal end of the femur and severing a small piece of the posterior portion of the pair of condyles. The preliminary rough cut is made prior to the step of resecting the tibia and after the step of resecting the distal end of the femur.

In one aspect, the rough cut guide includes a body having a proximal side, a distal side opposite the proximal side, an anterior edge, and a posterior edge. A pair of feet members extends from the proximal side adjacent the posterior edge. The pair of feet is aligned along a first plane and the feet are spaced apart from one another. A pair of saw slots extends through the body from the proximal side to the distal side. The pair of saw slots is aligned along a second plane and the slots are spaced apart from one another. The first plane defines an angle relative to the second plane, the angle being equal to the desired external rotation such that external rotation is established prior to tibia resecting. The step of making a preliminary rough cut includes positioning the guide on the femur such that the pair of feet members seats against the posterior portion of the pair of condyles and the proximal side abuts the resected distal end of the femur.

In another aspect, the method also includes the step of finishing the femur by severing and removing a final piece of the posterior portion of the pair of condyles. The small piece removed in the preliminary rough cut step is sized to preserve enough of posterior portion to permit the removal of the final piece.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 9 is a distal view of the rough cut guide of FIG. 8, installed on the distal end of the femur;

FIG. 10 is another perspective view of the rough cut guide of FIG. 8, installed on the distal end of the femur;

Figure 1:
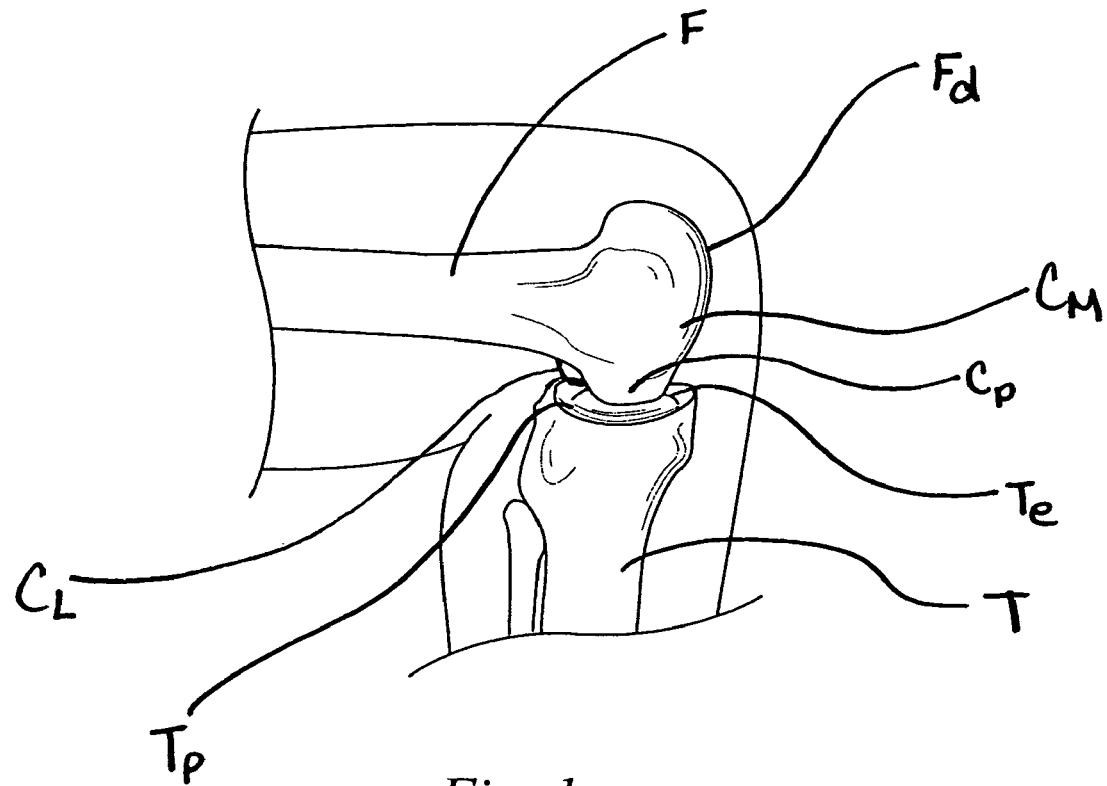
FIG. 1 is a medial aspect of a knee joint in 9020 flexion.

Corresponding reference characters indicate corresponding parts throughout the several views. Although the drawings represent embodiments of the present invention, the drawings are not necessarily to scale and certain features may be exaggerated in order to better illustrate and explain the present invention. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments hereinafter disclosed are not intended to be exhaustive or limit the invention to the precise forms disclosed in the following description. Rather the embodiments are chosen and described so that others skilled in the art may utilize its teachings.

Referring first to FIG. 1, a knee joint is illustrated including femur F and tibia T. Femur F includes a distal end having a pair of condyles including medial condyle $C_M$ (medial meaning located near the median or midsagittal plane) and lateral condyle $C_L$ (lateral meaning located near the side of the body or furthest from the median plane). Tibia T includes tibia plateau $T_P$, which mates with condyles $C_M$, $C_L$ and provides a surface upon which condyles $C_M$, $C_L$ can articulate during movement of the knee. As illustrated in FIG. 1, condyles $C_M$, $C_L$ each include posterior portion $C_P$ (posterior meaning located near the back of the body) which mates with tibial plateau $T_P$ when the knee joint is in 90° flexion. Tibial plateau $T_P$ includes tibial eminence or crest $T_e$ which extends superiorly from tibial plateau $T_P$ and fits within the intercondylar notch (not shown).

Minimally invasive methods for total knee arthroplasty (knee replacement) according to one embodiment of the present invention may first involve preoperative templating and/or sizing of femur F. Such preoperative procedures serve to estimate the size of the femoral component of the implant. Preoperative templating and sizing may be performed using any technique, including that described in The Zimmer MIS™ Quad-Sparing™ Surgical Technique for Total Knee Arthroplasty (NEXGEN® Complete Knee Solution), a surgical procedure for minimally invasive knee arthroplasty available from The Zimmer Institute of Warsaw, Ind., attached hereto as Appendix A and hereby incorporated by reference. Such techniques may include, for instance, taking radiographs of the knee, particularly the femur, and superimposing various template overlays over the radiographs to find the most ideal match. The template overlays correspond to various femoral component sizes.

Next, a minimal incision is defined and made according to conventional methods to provide access to, and expose, the knee joint. This minimal incision may be made according to the method described in The Zimmer MIS™ Quad-Sparing™ Surgical Technique, which describes making a medial parapatellar incision. Such an incision provides a medial approach to the knee joint. To facilitate an understanding of the present invention, the methods and devices of the present invention will now be described for use in a medial approach procedure. However, it should be understood that the methods and devices of the present invention could be adapted for use in various other minimally invasive approaches including a lateral approach. Furthermore, the methods and devices of the present invention could be adapted for use in standard open-incision procedures.

Figure 8:
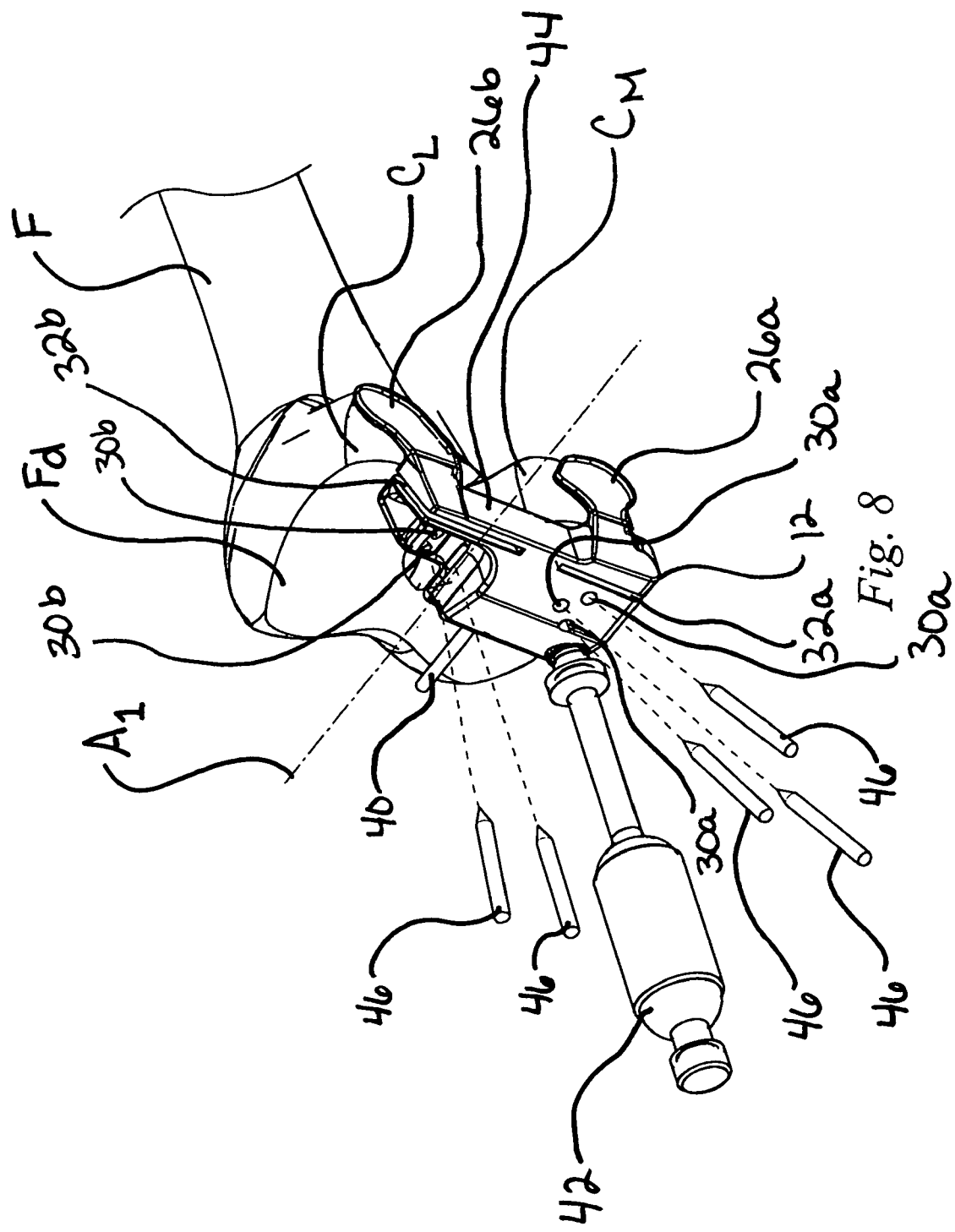
FIG. 8 is a perspective view of the rough cut guide of FIG. 4 installed on the distal end of a resected femur.

Reference points and lines, such as the Anterior/Posterior (A/P) axis (a.k.a. Whiteside's line), may be marked on femur F. As illustrated in FIG. 8, the A/P axis $A_1$ is a line extending anterior to posterior across distal end of the femur midway between condyles $C_M$, $C_L$. Distal end $F_d$ (FIG. 2) of femur F is then resected according to methods and using tools such as those described in The Zimmer MIS™ Quad-Sparing™ Surgical Technique.

Figure 2:
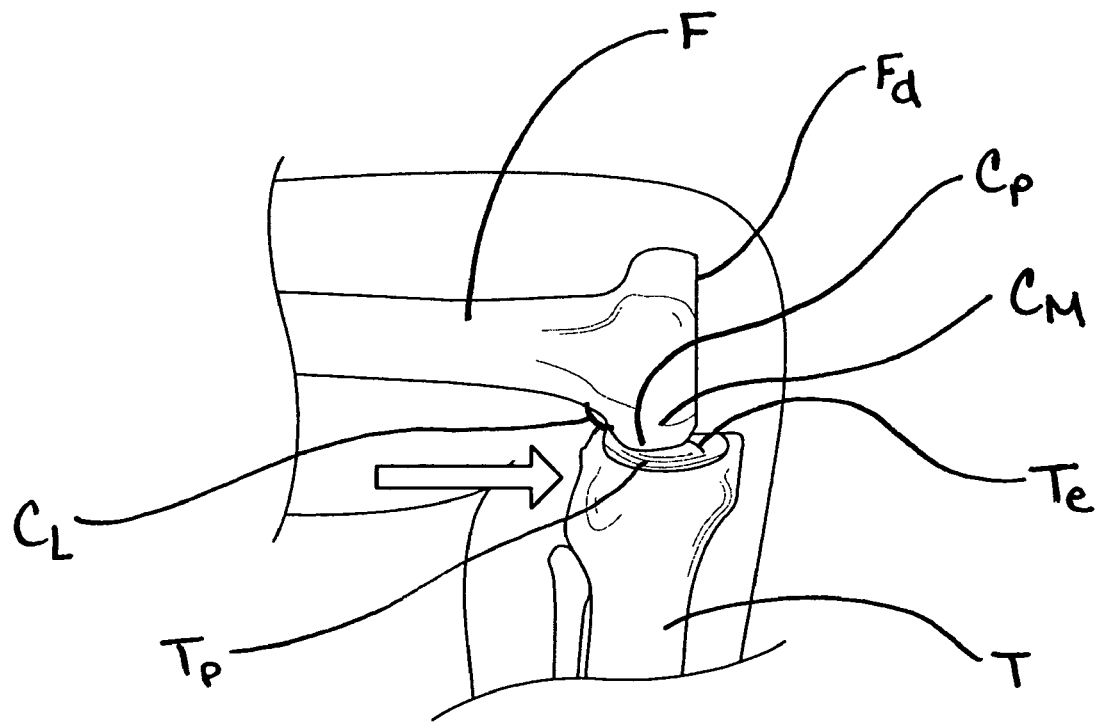
FIG. 2 is a medial aspect of the knee joint of FIG. 1 in 90° flexion wherein the distal end of the femur has been resected and the tibia is in partial subluxation.

Typically, tibia T is then resected using any methods and tools, for example, those described in The Zimmer MIS™ Quad-Sparing™ Surgical Technique. As illustrated in FIG. 2, to access the proximal end of tibia T, the tibia may be subluxed (dislocated) from the joint by moving the tibia outward in the direction of the arrow. However, subluxation of the tibia may be difficult to achieve because the rim or edge of tibial plateau may collide with posterior condylar portion $C_p$. In addition, the restricted space in the joint may make it difficult to remove the portion of tibial plateau cut during the resecting step.

Figure 3:
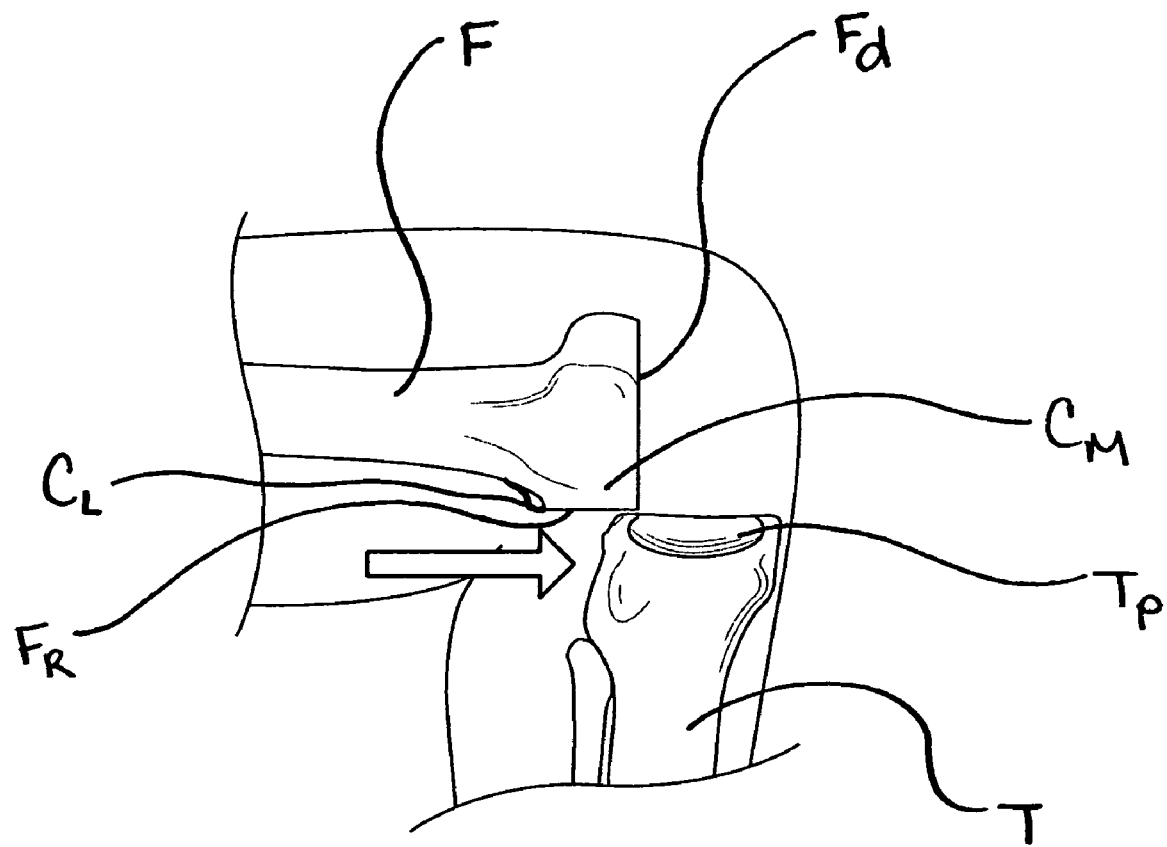
FIG. 3 is a medial aspect of the knee joint of FIG. 2 in 90° flexion wherein the posterior portion of the femoral condyles have been rough cut according to one embodiment of the present invention and the tibia is in subluxation from the joint.

Referring now to FIG. 3, to facilitate the tibia resecting step, a rough cut or preliminary cut of the posterior portion $C_p$ (FIGS. 1 and 2) on condyles $C_M$, $C_L$ is made prior to resecting tibia T. This rough cut removes a small amount of posterior condylar portion $C_p$ (FIGS. 1 and 2) to create more space in the joint thereby providing improved visibility of the surgical site and improved laxity in the joint. As illustrated in FIG. 3, the preliminary rough cut improves maneuverability of the joint to facilitate subluxation of tibia T and, ultimately, eases the resecting of tibia T and the removal of cut portions of tibial plateau $T_P$. Although this embodiment describes the rough cut being made after resecting the femur, the rough cut could be made prior to resecting the femur.

Referring now to FIGS. 4-12 an exemplary process and device for making the rough cut will now be described. FIGS. 4-7 illustrate preliminary rough cut guide 10 which may be used to make the rough cut of posterior condylar portion $C_P$ (FIGS. 1 and 2). Rough cut guide 10 includes body 12 having proximal bone-bearing side 14 and distal side 16 disposed opposite proximal side 14. Body 12 further includes posterior edge 18, anterior edge 20, medial end 22 and lateral end 24, each of which extend between proximal side 14 and distal side 16.

Figure 4:
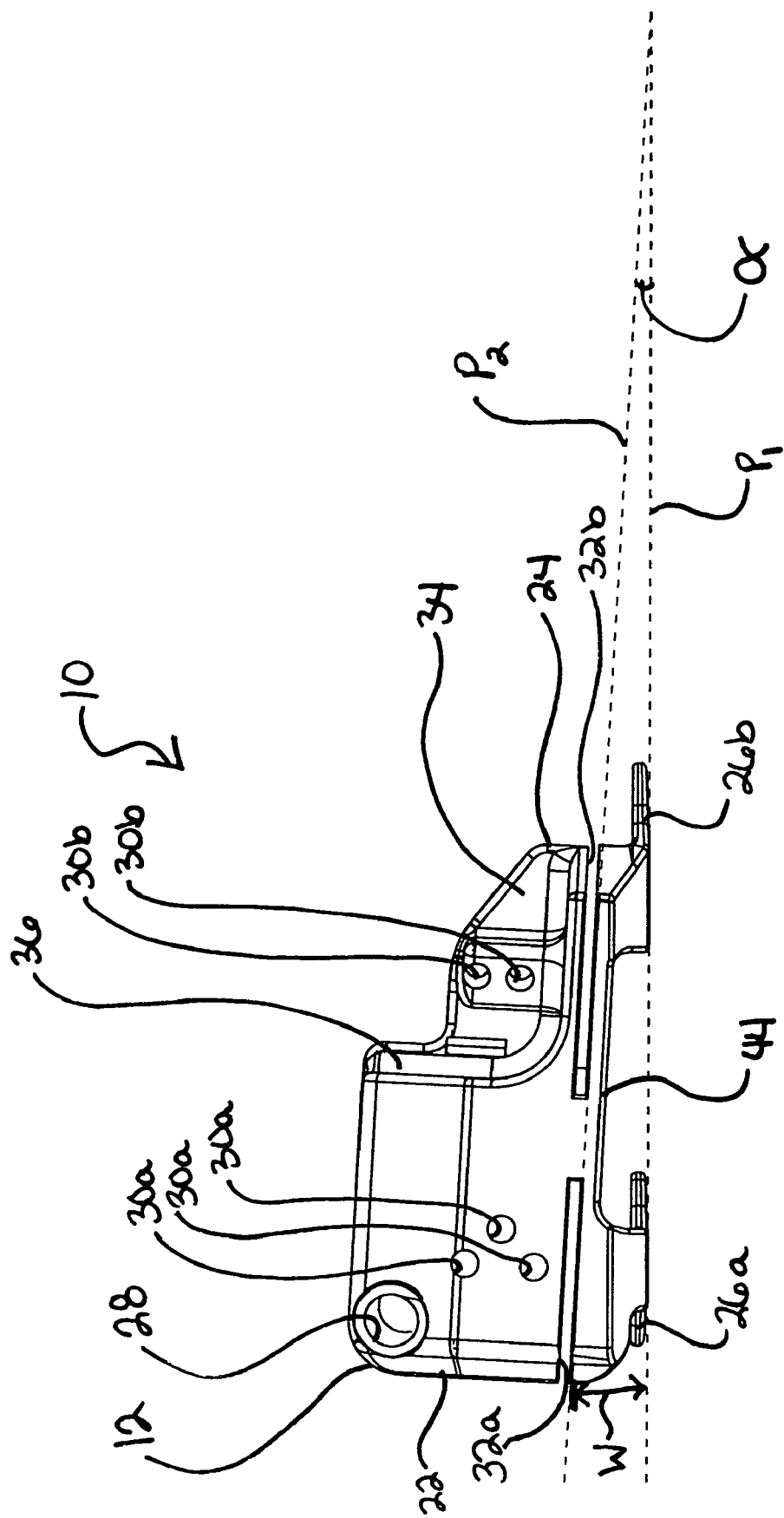
FIG. 4 is a distal perspective view of a posterior rough cut guide according to one embodiment of the present invention.
Figure 5:
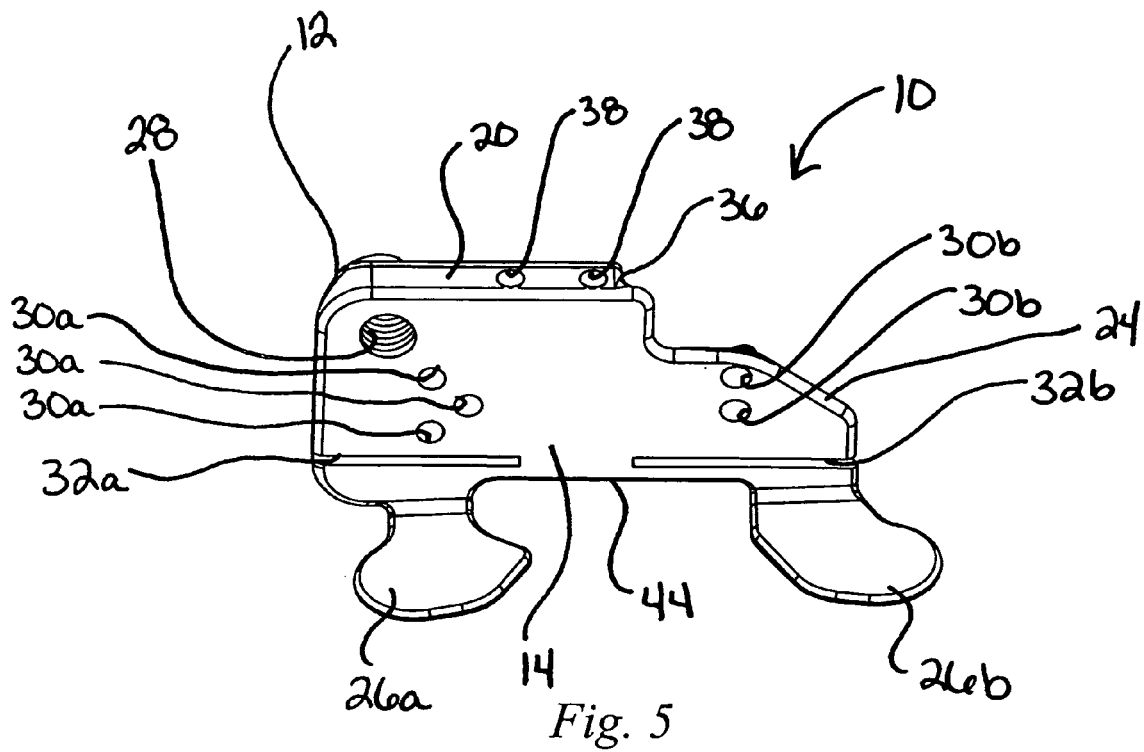
FIG. 5 is a proximal perspective view of the rough cut guide of FIG. 4.
Figure 7:
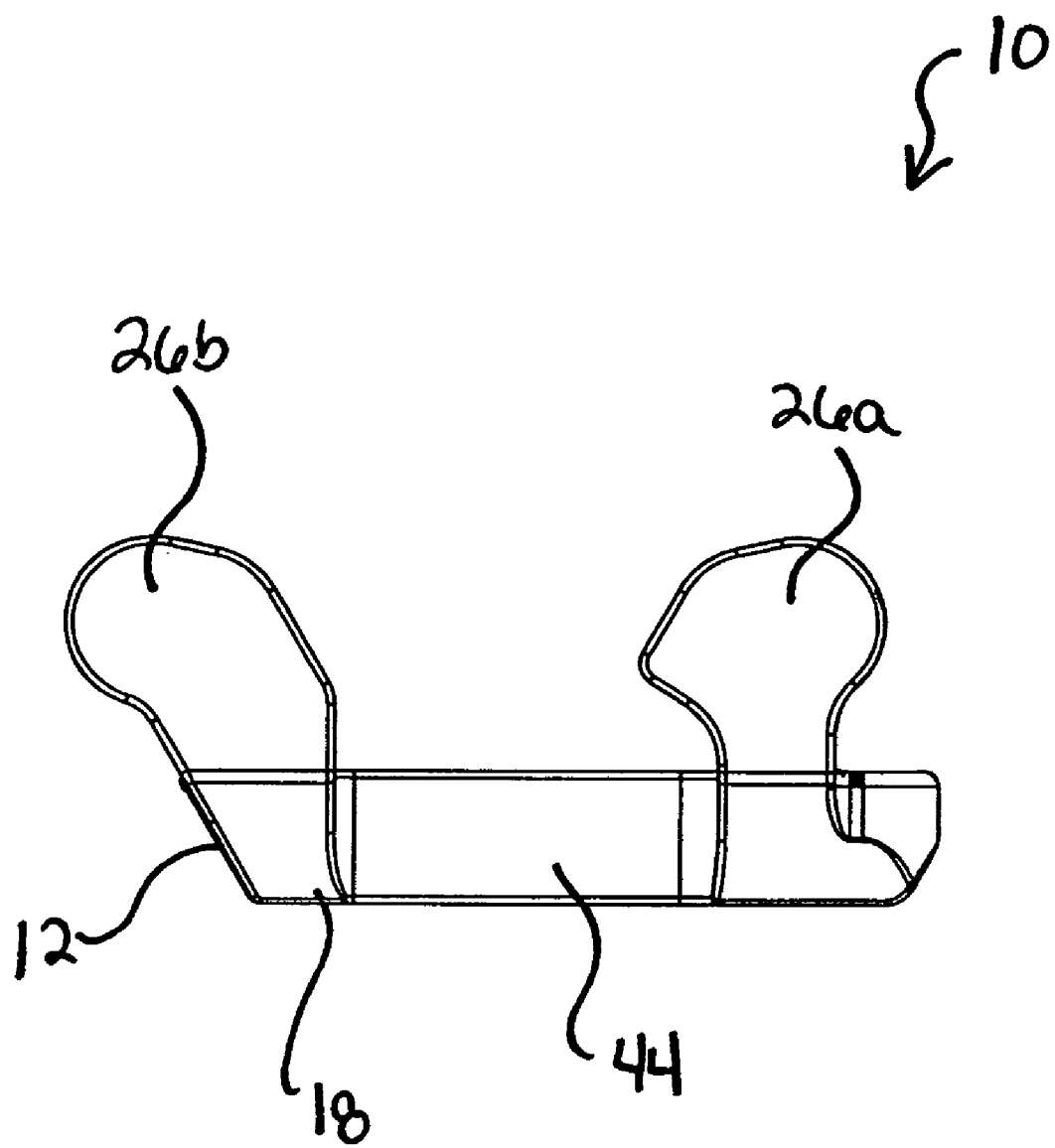
FIG. 7 is a posterior edge view of the rough cut guide of FIG. 4.

A pair of paddle feet members (26a, 26b) extend from proximal side 14 adjacent posterior edge 18. Paddle feet members include medial foot member 26a and lateral foot member 26b. Referring specifically to FIGS. 4, 5 and 7, medial and lateral feet 26a, 26b are spaced apart from one another and intercondylar recess 44 is defined in posterior edge 18 between medial and lateral feet 26a, 26b. Feet 26a and 26b are aligned along a line or plane $P_1$.

Turning now to FIGS. 4 and 5, body 12 includes handle receiving opening 28, which may be threaded to receive threaded handle 42 (FIG. 8) as described in further detail below. Body 12 also includes fastener receiving openings 30a, 30b extending through body 12 from proximal side 14 to distal side 16. Fastener openings 30a, 30b are adapted to receive fasteners 46 (FIG. 8) as further described below. Fastener receiving openings 30a are medially positioned in body 12 (i.e. nearer medial end 22 than lateral end 24), while fastener receiving openings 30b are laterally positioned in body 12. Lateral fastener openings 30b may be angled in medial to lateral direction moving from distal side 16 to proximal side 14 to facilitate medial access to, and insertion of fasteners through, openings 20b.

Referring still to FIGS. 4 and 5, body 12 also includes a pair of saw receiving slots 32a, 32b, spaced apart from one another and each extending through body 12 from proximal side 14 to distal side 16. Saw slot 32a extends from medial end 22 inwardly toward the center of body 12, while slot 32b extends from lateral end 24 inwardly toward the center of body 12. As described in further detail below, saw slots 32a, 32b are adapted to receive and guide saw S (FIG. 10) and are sized to permit saw S to sever a small amount of posterior condylar portion $C_P$ of each of medial and lateral condyles $C_M$, $C_L$.

Saw slots 32a, 32b are positioned along line or plane $P_2$. Saw slot plane $P_2$ defines an angle $\alpha$ relative to feet plane $P_1$. Angle $\alpha$ is equal to the desired external rotation. For example, angle $\alpha$ may equal 3°, which is a common desired angle $\alpha$. Saw slots 32a, 32b are also spaced apart from feet 26a, 26b, respectively, to provide a desired depth of cut. For instance, width W is the distance between medial foot 26a and medial saw slot 32a. Width W determines the amount or depth of the posterior condylar portion $C_P$ that will be cut from medial condyle $C_M$. Width W may be sized to provide any depth of cut, which would free up space within the joint while leaving enough of posterior condylar portion $C_P$ to allow the final finishing cuts. Such cut depths may depend on a variety of factors including the size of the femur, and the size, style, and manufacturer of the femoral component. Rough cut guide 10 may also be designed with a plurality of different cut widths W and/or angles $\alpha$ to achieve desired cut depths and external rotations.

Figure 6:
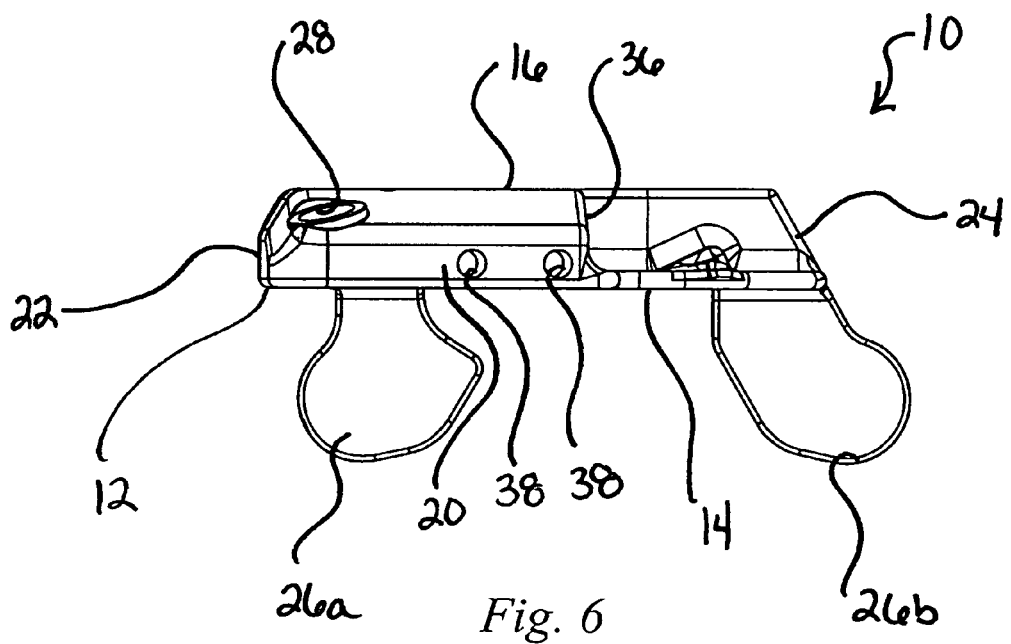
FIG. 6 is an anterior edge view of the rough cut guide of FIG. 4.

Referring now to FIGS. 4 and 6, body 12 is contoured to facilitate insertion and positioning of rough cut guide 10 in the joint. Particularly, distal side 16 of body 12 includes patellar clearance recess portion 34 extending from lateral end 24 to near the center of body 12 such that the lateral portion of body 12 has a reduced thickness (measured from proximal side 14 to distal side 16) relative to that of the medial portion of the body. Patellar clearance recess portion 34 forms alignment ridge 36, which, as discussed further below, may be positioned to provide a guide for the alignment of body 12 on femur F.

Turning now to FIGS. 5 and 6, anterior edge 20 includes alignment pin openings 38, which are adapted to receive alignment pin 40 (FIG. 8) as further described below.

Referring to FIGS. 8-12, the step of making a preliminary rough cut of posterior condylar portion $C_P$ using rough cut guide 10 will now be described. First, as shown in FIG. 8, threaded handle 42 is screwed into threaded handle receiving opening 28 (FIG. 4) in body 12. With the knee in approximately 90° flexion, body 12 is inserted into the joint space using handle 42. Body 12 is positioned on distal end $F_d$ of femur F such that proximal side 14 seats against distal end $F_d$ and medial and lateral feet 26a, 26b are contacting the most prominent points of medial and lateral condyles $C_M$, $C_L$, respectively. The preliminary rough cut procedure could be adapted to be performed with the knee in angles of flexion or in extension. To ease insertion and positioning of body 12, tibial eminence $T_e$ (FIGS. 1 and 2) may be cut free hand. As mentioned above, body 12 may be contoured to facilitate insertion and positioning of body 12. For instance, posterior edge 18 includes intercondylar recess 44 in the space between feet 26a, 26b. Intercondylar recess 44 provides a clearance area that helps body 12 clear tibial eminences $T_e$ during insertion. Furthermore, distal side 16 includes patellar clearance portion 34, which provides body 12 with reduced thickness in the lateral portion. Patellar clearance portion 34 facilitates insertion of body 12 beneath the patella (not shown) from a medial approach with minimal disruption from, and injury to, the patella (not shown), patella tendon, and/or other soft tissues.

Body 12 may be configured such that when medial and lateral feet 26a, 26b are contacting the most prominent portions of posterior condylar portion $C_P$ of medial and lateral condyles $C_M$, $C_L$, in many cases, body 12 will be properly aligned to achieve the desired cuts and external rotation. However, in cases where medial and/or lateral condyles $C_M$, $C_L$ are damaged, deteriorated or abnormal, verification and modification of alignment may be desired.

To this end, alignment ridge 36 may be configured to serve as an alignment guide. As illustrated in FIG. 8, alignment may be verified by aligning ridge 36 with Anterior/Posterior (A/P) axis $A_1$, previously identified and marked on the distal end $F_d$ of femur F. Alternatively, or in addition, alignment pin 40 may be inserted into any of alignment pin openings 38 such that pin 40 extends from anterior edge 20. To verify alignment of cut guide 10, pin 40 is compared to A/P axis $A_1$. Pin 40 and openings 38 are designed such that pin 40 should extend parallel to A/P axis $A_1$ when cut guide 10 is aligned in the desired position. If rotational adjustment of cut guide 10 is desired, body 12 may be rotated such that either of feet 26a, 26b is spaced from respective condyles $C_M$, $C_L$.

Referring still to FIG. 8, once cut guide 10 is aligned, fasteners 46 are inserted through fastener openings 30a, 30b and into distal end $F_d$ of femur F to secure guide 10 to femur F. Fasteners 46 may be any fasteners suitable for securing cut guide 10 to femur F including screws, rods, pins and nails. Furthermore, while FIG. 8 shows a fastener inserted into each of openings 30a, 30b, any number of fasteners may be used and body 12 may include any number of openings.

Figure 11:
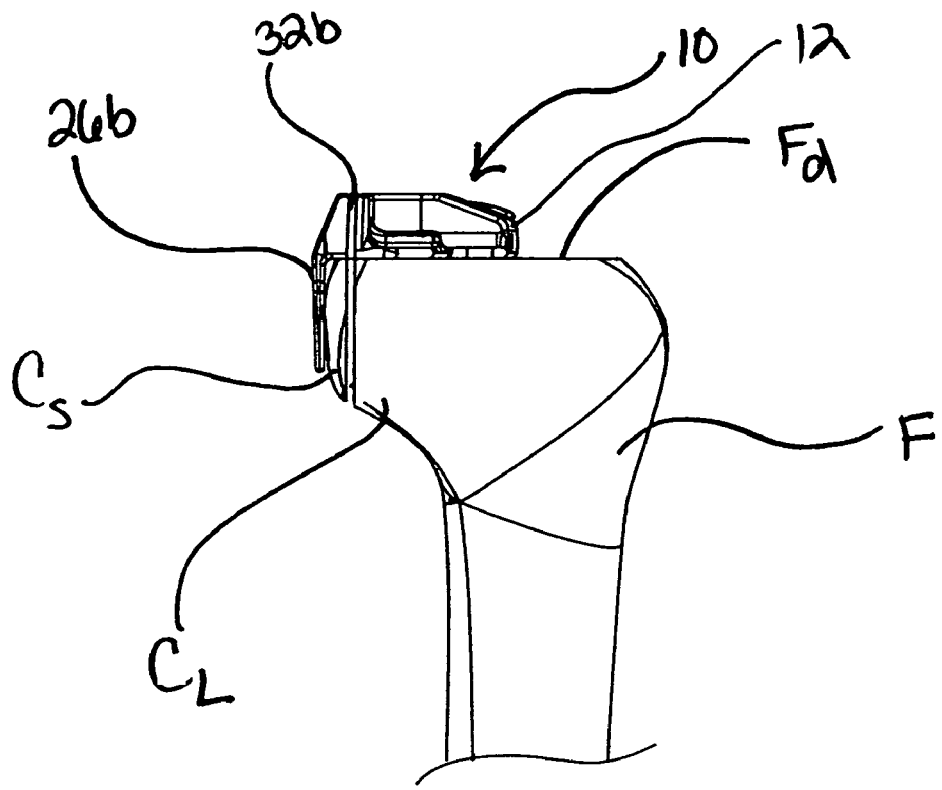
FIG. 11 is a lateral aspect of the rough cut guide of FIG. 8, installed on the distal end of the femur, wherein the rough cut has been performed.
Figure 12:
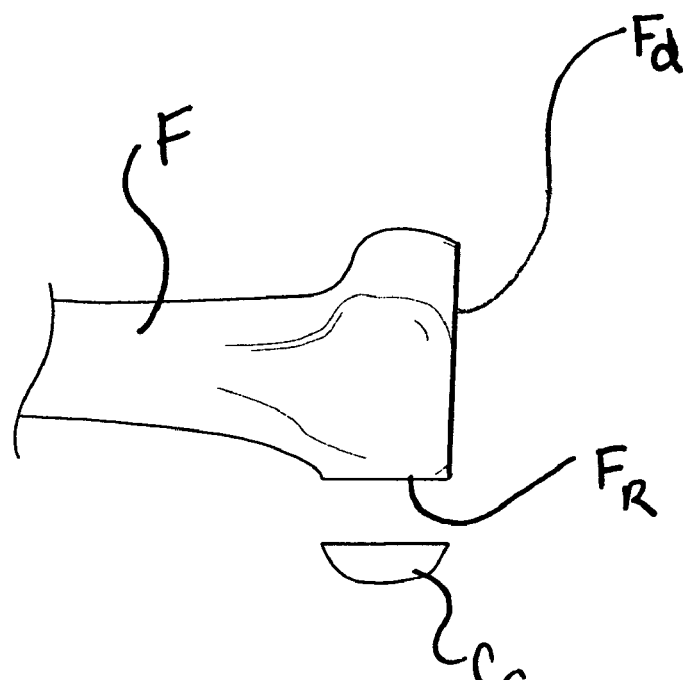
FIG. 12 is a lateral aspect of the femur shown in FIG. 11 wherein the rough cut guide has been removed.
Figure 13:
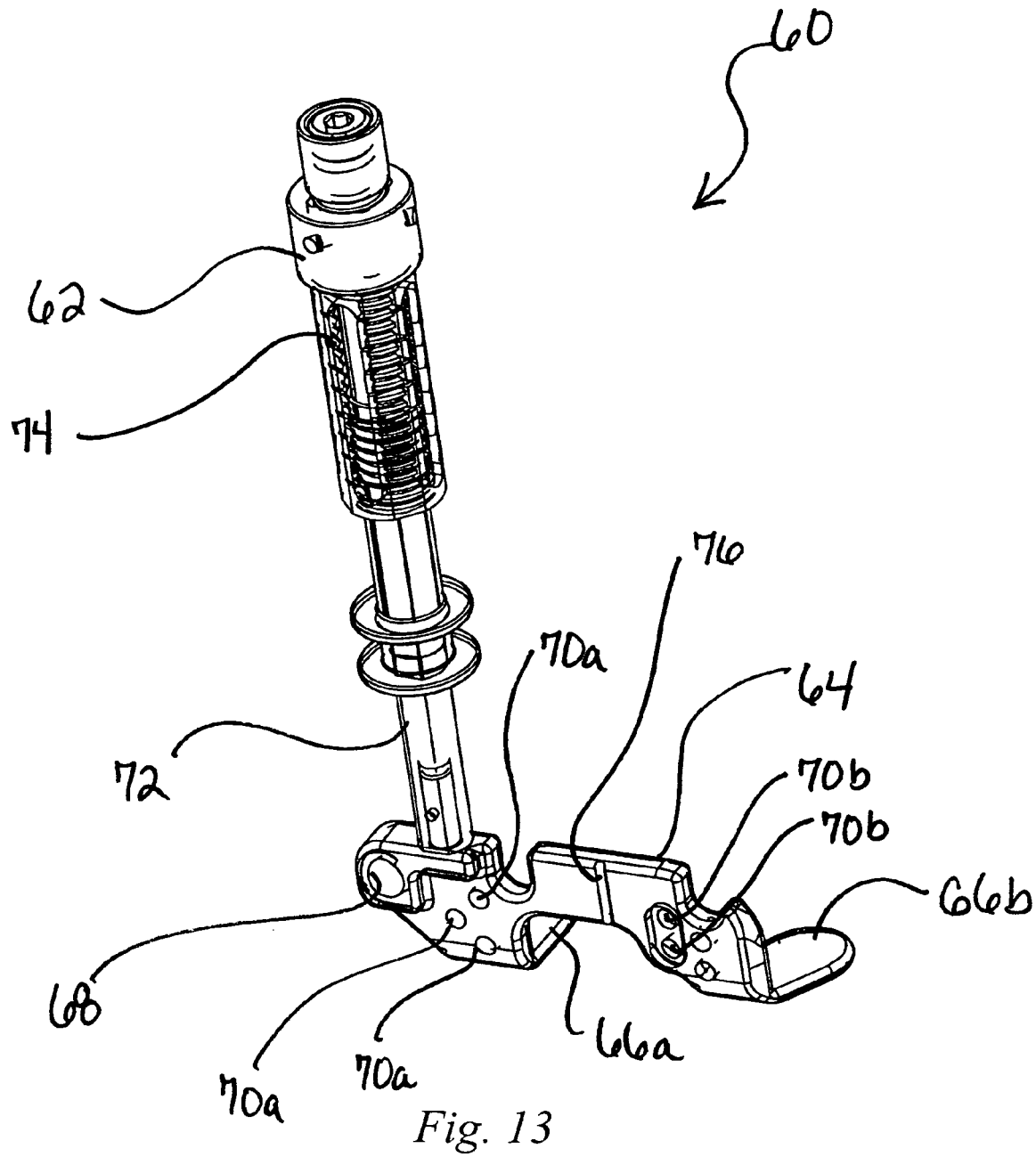
FIG. 13 is a distal perspective view of a sizer assembly according to one embodiment of the present invention.
Figure 14:
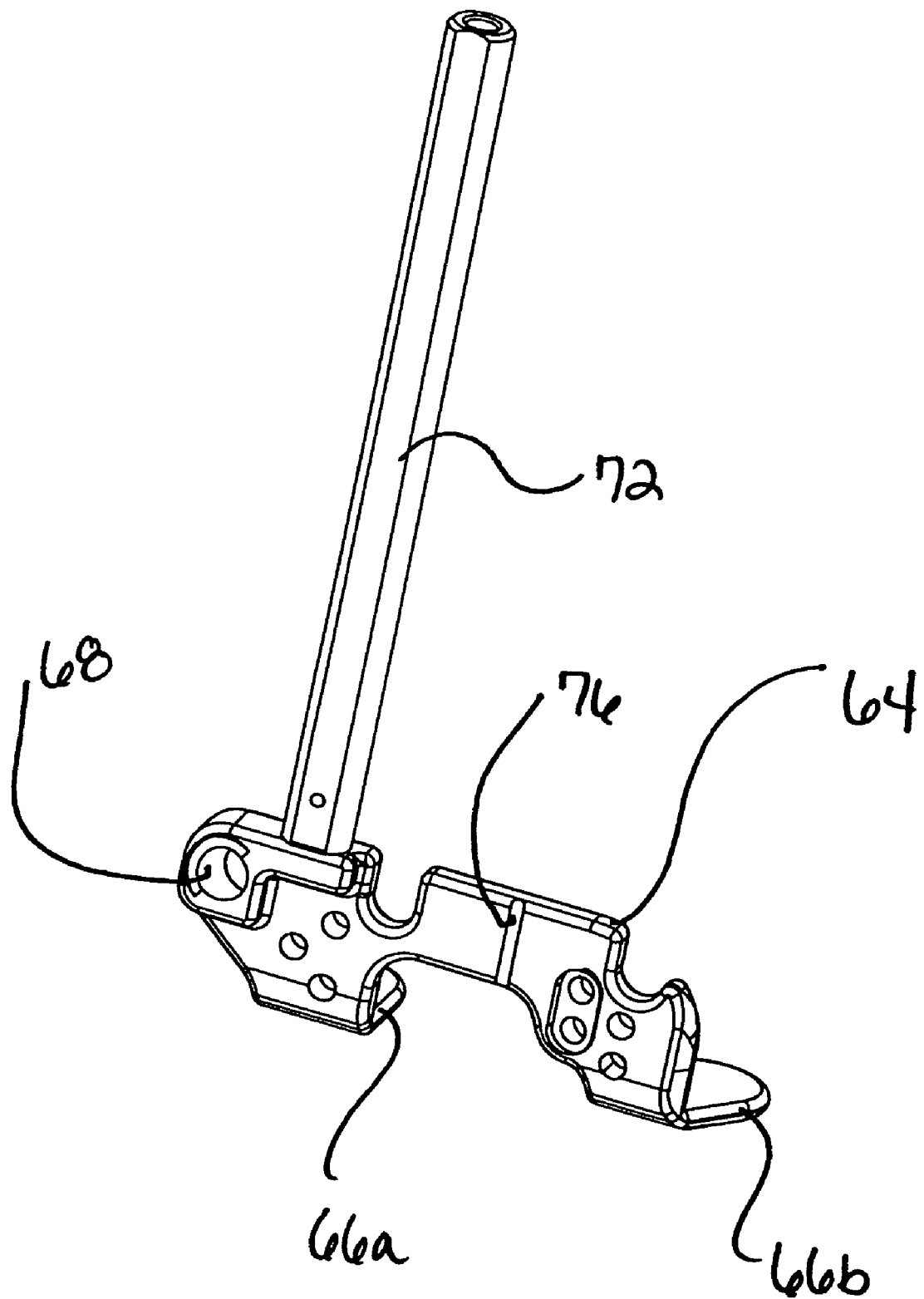
FIG. 14 is a distal perspective view of the sizer base of the sizer assembly of FIG. 13.
Figure 15:
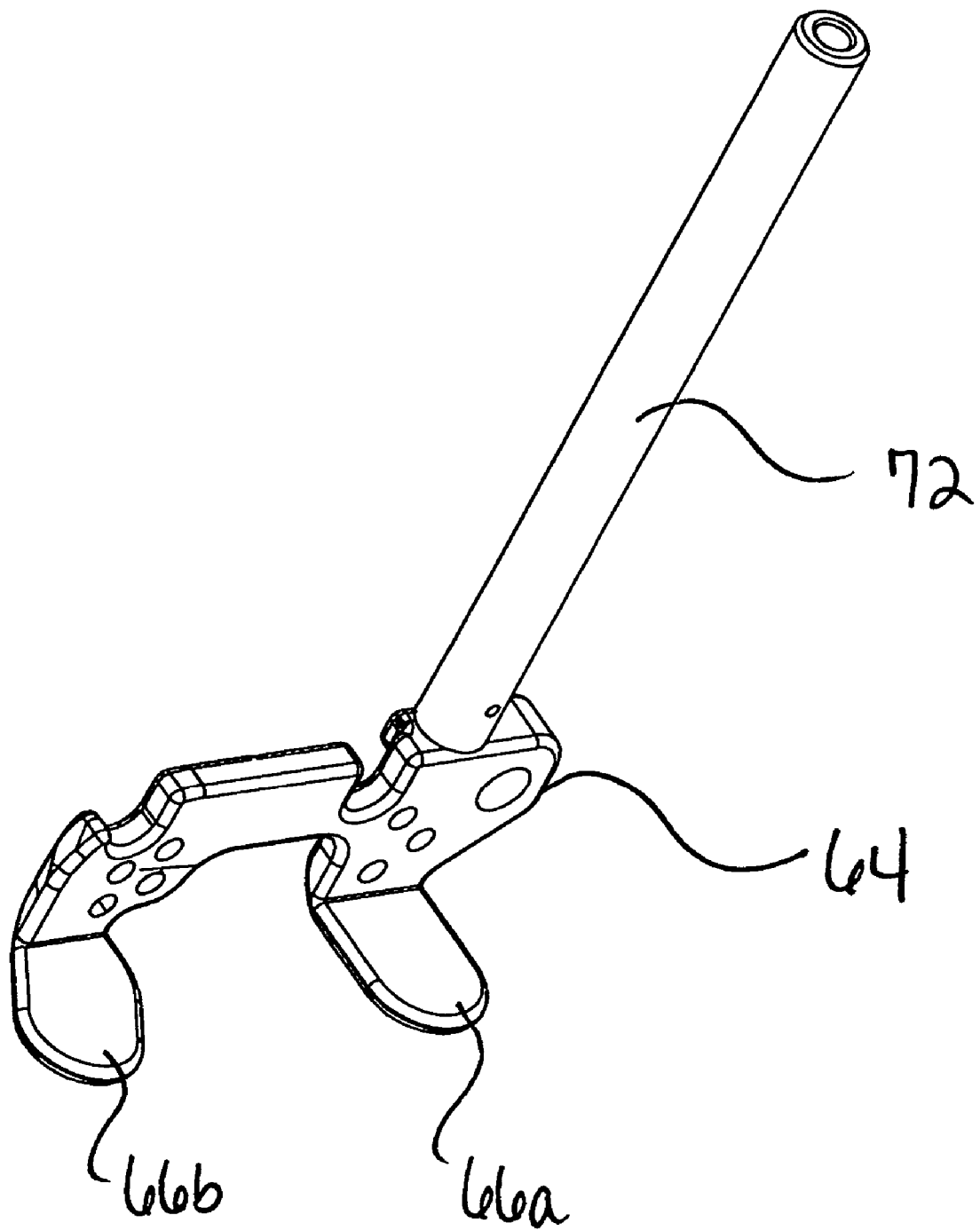
FIG. 15 is a proximal perspective view of the sizer base of FIG. 14.
Figure 16:
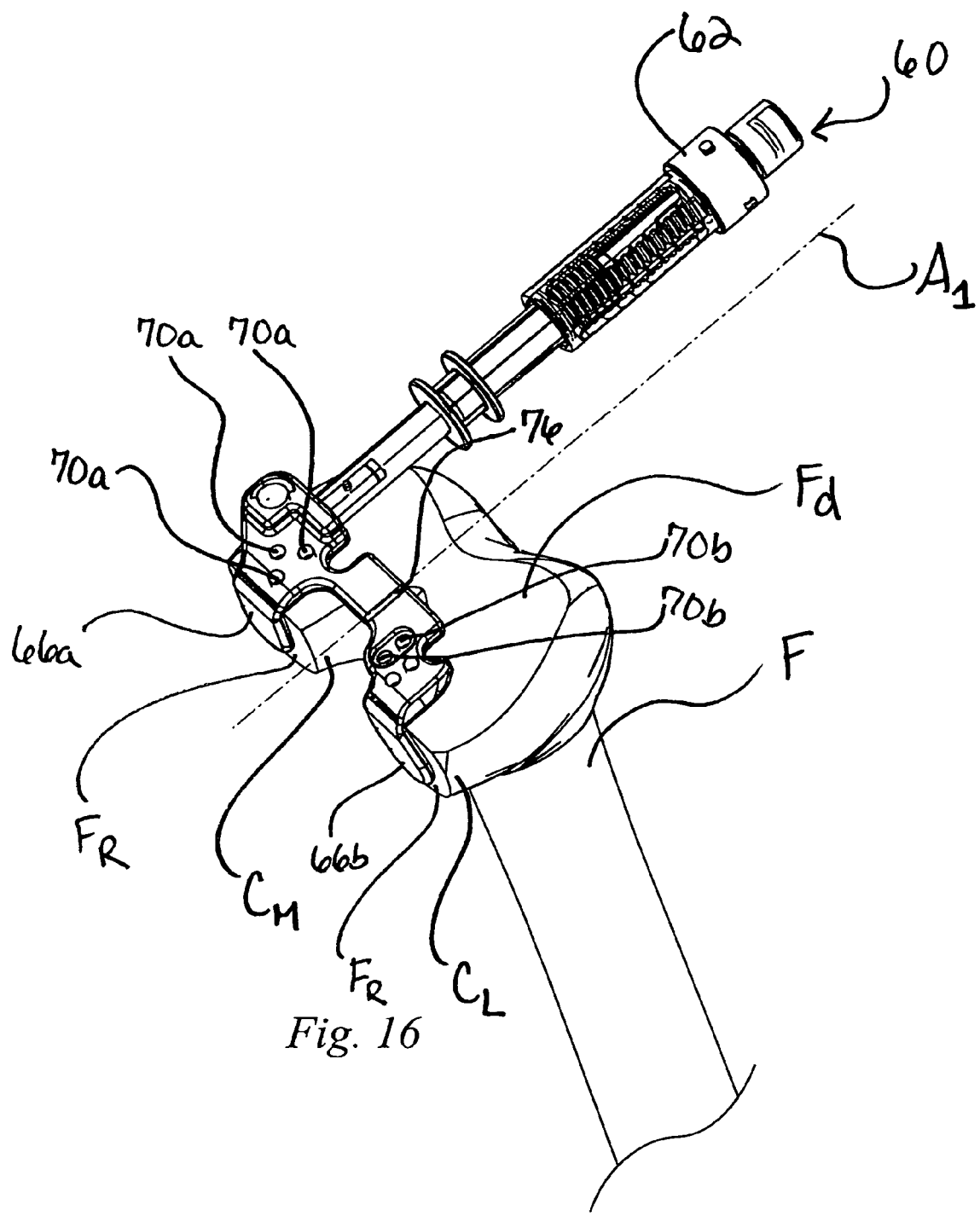
FIG. 16 is a perspective view of the sizer assembly of FIG. 13 installed on the distal end of the femur of FIG. 12.

Turning now to FIGS. 9-11, once cut guide 10 is secured to femur F, handle 42 (FIG. 8) is removed. Saw blade S is inserted through slots 26a, 26b and is used to sever a portion of posterior condylar portion $C_P$ from condyles $C_M$, $C_L$, respectively. Next, fasteners 46 and cut guide 10 are removed from femur F. As shown in FIG. 12, severed portions $C_S$ of condyles $C_M$, $C_L$ are removed leaving a rough cut posterior surface $F_R$. As a result, more joint space is available for improved visibility of the surgical site and increased laxity of the joint. As shown in FIG. 3, subluxation of tibia T is more easily achieved because posterior condylar portion $C_P$ no longer collides with the rim of tibial plateau $T_P$. In addition, external rotation is established earlier in the procedure and provides an additional reference point/surface for remaining cuts. The proximal end of tibia T may now be resected according to techniques such as those described in The Zimmer MIS™ Quad-Sparing™ Surgical Technique (Appendix A).

It should be understood that cut guide 10 illustrated in FIGS. 4-8 is a left medial guide adapted for use in a medial approach of the left leg. The present invention contemplates a second, right medial guide for use in a medial approach of the right leg. Furthermore, the cut guide and method may be adapted for use in other approaches including a lateral approach. Guide 10 may be formed of any surgical grade material capable of guiding and withstanding movement of saw S. For example, guide 10 may be formed of stainless steel or titanium.

After tibia T is resected, femur F is sized according to techniques and using tools such as those disclosed in The Zimmer MIS™ Quad-Sparing™ Surgical Technique (Appendix A). However, if guide 10 was configured to provide the desired external rotation, the conventional sizer assembly (which typically is configured to provide the desired external rotation) should be modified.

Referring to FIGS. 12-16, sizer assembly 60 generally includes sizer tower 62 and sizer base 64. Sizer base 64 includes feet 66a, 66b extending proximally from base 64 and configured to bear against rough cut surface $F_R$ of medial and lateral condyles, respectively. Sizer base 64 includes base rod 72 extending anteriorly from base 64. Handle receiving opening 68 is defined in base 64 and is adapted to receive handle 42 (FIG. 8). Fastener receiving openings 70 extend through base 64 and are adapted to receive fasteners 46. Base 64 includes an alignment etch 76 in the distal surface of base 64. Alignment etch 76 is adapted to align with A/P axis $A_1$ when base 64 is properly positioned. Sizer tower 62 is adapted to fit on base rod 72 and includes a series of measurement markings 74 corresponding to implant sizes. Because external rotation has already been established using cut guide 10, sizer base 64 is configured to provide 0° of additional external rotation. Sizer base 64 is secured to femur F and sizer tower 62 measures femur F using conventional techniques.

The remaining steps in minimally invasive arthroplasty, such as finishing the femur, sizing and finishing the tibia, performing trial reductions, and implanting components, may be performed using conventional techniques such as those disclosed in The Zimmer MIS™ Quad-Sparing™ Surgical Technique. For instance, the step of finishing the femur may include making a final cut of the posterior portion of the femoral condyles, as well as, making anterior cuts and chamfer cuts of the distal end of the femur. Alternatively, or in addition, the remaining steps and the prostheses implanted in this method may include features which are similar to the techniques, methods, and implants disclosed in U.S. Pat. Nos. 6,485,519 and 6,719,800, entitled CONSTRAINED PROSTHETIC KNEE WITH ROTATING BEARING; U.S. patent application Ser. No. 10/357,991, entitled SIZING PLATE AND SIZING PLATE EXTRACTION, filed on Feb. 4, 2003; U.S. patent application Ser. No. 10/305,697, entitled METHOD AND APPARATUS FOR ACHIEVING CORRECT LIMB ALIGNMENT IN UNICONDYLAR KNEE ARTHROPLASTY, filed on Nov. 27, 2002; and U.S. patent application Ser. No. 11/047,205 entitled "APPARATUS AND METHOD FOR SIZING A DISTAL FEMUR", filed on Jan. 28, 2005, each assigned to the assignee of the present invention, the disclosures of which are expressly incorporated herein by reference.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical method for preparing a knee joint to receive the components of a knee prosthesis, the knee joint includes a femur having a pair of condyles at a distal end, and a tibia having a tibial plateau at a proximal end, the method comprising the steps of:

exposing the joint;

resecting the distal end of the femur by cutting and removing a distal portion of the pair of condyles;

prior to performing an initial resection of the tibial plateau and after resection of the distal end of the femur, making a preliminary rough cut of a posterior portion of the pair of condyles of the femur by severing and removing a piece of the posterior portion of the pair of condyles, wherein the piece of the posterior portion removed is sized to preserve enough of the posterior portion of the condyles to permit a final cut;

resecting the tibia by cutting and removing a proximal portion of the tibial plateau, the step of resecting the tibia performed after the step of making a preliminary rough cut of a posterior portion of the pair of condyles of the femur; and after the step of resecting the tibia, finishing the femur by making a final cut of the posterior portion of the pair of condyles.

2. The method of claim 1 further comprising the step of marking an A/P axis on the distal end of the femur.

3. The method of claim 1 wherein the step of making a preliminary rough cut includes positioning a rough cut guide on the distal end of the resected femur.

4. The method of claim 3 wherein the rough cut guide comprises:

a body having a proximal side, a distal side opposite said proximal side, an anterior edge, and a posterior edge;

a pair of feet members extending from said proximal side adjacent said posterior edge, said pair of feet aligned along a first plane, said pair of feet members spaced apart from one another;

a pair of saw slots extending through said body from said proximal side to said distal side, said pair of saw slots aligned along a second plane; said pair of slots spaced apart from one another and configured to extend over the pair of condyles; and wherein the step of making a preliminary rough cut includes positioning the guide on the femur such that the pair of feet members seats against the posterior portion of the pair of condyles and the proximal side abuts the resected distal end of the femur.

5. The method of claim 4 wherein said first plane defines an angle relative to said second plane, said angle being equal to a desired external rotation.

6. The method of claim 4 wherein said body includes a first end and a second end, said distal side of said body includes a patellar clearance recess extending inwardly from said first end to produce a portion having a reduced thickness extending between distal and proximal sides.

7. The method of claim 6 wherein said first end is a medial end and said second end is a lateral end.

8. The method of claim 6 wherein said first end is a lateral end and said second end is a medial end.

9. The method of claim 4 wherein the cut guide includes at least one alignment feature, and the method further comprises the steps of:

marking the A/P axis on the distal end of the femur; and verifying the alignment of the cut guide by comparing the at least one alignment feature to the A/P axis.

10. The method of claim 9 wherein the alignment feature includes an alignment pin received within an opening defined in the anterior edge.

11. A surgical method for preparing a knee joint to receive the components of a knee prosthesis, the knee joint includes a femur having a pair of condyles at a distal end, and a tibia having a tibial plateau at a proximal end; the method comprising the steps of:

exposing the joint;

resecting the distal end of the femur;

prior to performing an initial resection of the tibial plateau, making a preliminary rough cut of a posterior portion of the pair of condyles by severing and removing a small piece of the posterior portion of the pair of condyles, the step of making a preliminary rough cut performed prior to the step of resecting the tibial plateau and after the step of resecting the distal end of the femur, the preliminary rough cut yielding a rough cut surface;

resecting the tibia plateau; and after the step of resecting the tibial plateau, finishing the femur by severing and removing a final piece of the posterior portion of the pair of condyles, wherein the small piece removed in the step of making a preliminary rough cut is sized to preserve enough of the posterior portion to then permit the removal of the final piece.

12. The method of claim 11 wherein the step of making a preliminary rough cut includes positioning a cut guide on the distal end of the femur.

13. The method of claim 12 wherein the cut guide is adapted to establish a desired external rotation, such that the external rotation is established prior to the step of resecting the tibial plateau.

14. The method of claim 11 further comprising the step of sizing the femur using a sizer assembly, said sizer assembly adapted to use the rough cut surface as a reference surface.

15. A method of preparing the tibial proximal end and the distal end of the femur for the implantation of prosthetic components, the distal end including a pair of condyles, the method comprising the steps of:

exposing the joint;

resecting the distal end of the femur;

prior to performing an initial resection of the tibial plateau, making a preliminary rough cut of a posterior portion of the pair of condyles of the femur by positioning a cut guide on the distal end of the femur and severing a small piece of the posterior portion of the pair of condyles, said cut guide adapted to establish a desired external rotation, the step of making a preliminary rough cut performed prior to the step of resecting the tibial plateau and after the step of resecting the distal end of the femur, the preliminary rough cut yielding a rough cut surface;

resecting the tibial plateau; and after the step of resecting the tibial plateau, finishing the femur by severing and removing a final piece of the posterior portion of the pair of condyles, wherein the small piece removed in the step of making a preliminary rough cut is sized to preserve enough of the posterior portion to permit the removal of the final piece.

16. The method of claim 15 further comprising the step of sizing the femur using a sizer assembly, said sizer assembly adapted to use the rough cut surface as a reference surface.

* * * * *